United States Patent [19]

Wollweber et al.

[11] 4,287,199
[45] Sep. 1, 1981

[54] BENZIMIDAZOLYLCARBAMIC ACID ESTERS SUBSTITUTED ON THE BENZENOID NUCLEUS BY AN OXY OR THIO SUBSTITUENT

[75] Inventors: Hartmund Wollweber, Wuppertal; Heinrich Kölling, Haan; Herbert Thomas; Peter Andrews, both of Wuppertal, all of Fed. Rep. of Germany

[73] Assignee: Bayer Aktiengesellschaft, Leverkusen, Fed. Rep. of Germany

[21] Appl. No.: 83,883

[22] Filed: Oct. 11, 1979

[30] Foreign Application Priority Data

Oct. 19, 1978 [DE] Fed. Rep. of Germany ....... 2845537

[51] Int. Cl.$^3$ ................ A61K 31/445; A61K 31/415; C07D 235/32; C07D 401/12
[52] U.S. Cl. ................................. 424/267; 424/273 B; 546/199; 546/112; 546/134; 548/306; 544/132; 544/370
[58] Field of Search ................... 548/306; 424/273 B, 424/267; 546/199

[56] References Cited

U.S. PATENT DOCUMENTS

| | | | |
|---|---|---|---|
| 3,929,821 | 12/1975 | Beard et al. | 548/306 |
| 3,929,823 | 12/1975 | Beard et al. | 548/306 |
| 3,929,824 | 12/1975 | Beard et al. | 548/306 |
| 3,935,209 | 1/1976 | Beard et al. | 424/273 B |
| 3,969,526 | 7/1976 | Gyurik et al. | 548/306 |
| 4,025,638 | 5/1977 | Gyurik et al. | 424/273 B |
| 4,046,908 | 9/1977 | Haugwitz et al. | 548/306 |
| 4,093,732 | 6/1978 | Haugwitz et al. | 548/306 |
| 4,145,431 | 3/1979 | Haugwitz | 424/273 B |
| 4,174,400 | 11/1979 | Mrozik | 548/306 |
| 4,182,893 | 1/1980 | Piccardi et al. | 548/306 |

FOREIGN PATENT DOCUMENTS 2366069 10/1977 Fed. Rep. of Germany .......... 548/306

Primary Examiner—Henry R. Jiles
Assistant Examiner—Jane T. Fan
Attorney, Agent, or Firm—Sprung, Felfe, Horn, Lynch & Kramer

[57] ABSTRACT

The invention relates to 2-benzimidazolylcarbamic acid esters, substituted on the benzenoid nucleus by an aminoalkoxy, aminoalkylthio, an aminoalkylsulphinyl or an aminoalkylsulphonyl grouping. The invention also includes methods for making the compounds of the invention, compositions containing said compounds and the use of said compounds and compositions as anthelminitic agents.

10 Claims, No Drawings

BENZIMIDAZOLYLCARBAMIC ACID ESTERS SUBSTITUTED ON THE BENZENOID NUCLEUS BY AN OXY OR THIO SUBSTITUENT

The present invention relates to certain new 2-benzimidazolylcarbamic acid ester compounds, to processes for their production and to their use as anthelmintic agents.

It has already been disclosed that benzimidazolylcarbamic acid esters which, in the 5(6)-position, are either unsubstituted or substituted by substituents different from those of compounds of the present invention have an anthelmintic action (in this context, see DE-OS (German Published Specification) No. 2,029,637, French Patent Specification No. 1,556,824, DE-OS (German Published Specification) No. 2,164,690 and P. Actor et al., Nature 215, 321 (1967)). Thus, the benzimidazolylcarbamic acid esters Parbendazole (A) and Mebendazole (B) are commercial products for the same indication.

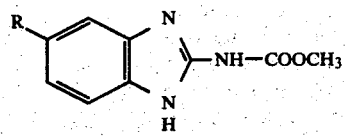

R = $C_4H_9$ = Parbendazole (A)
R = $COC_6H_5$ = Mebendazole (B)

However, these compounds have the disadvantage that they are sparingly soluble in water and other physiologically acceptable solvents and thus in practice cannot be used parenterally. Oily solutions or suspensions can indeed be prepared from them, but, for example when administered parenterally to large animals, these are not sufficiently active and/or are not tolerated locally.

However, parenteral administration of anthelmintic agents is of great economic importance for the treatment of numerous species of animals, in particular of large animals, such as cattle, and other warm-blooded animals.

According to the present invention there are provided compounds which are 2-benzimidazolylcarbamic acid esters of the formula

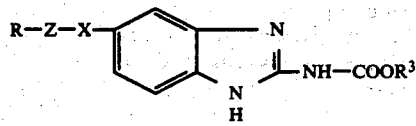

or a salt thereof in which
X denotes a sulphur atom, an oxygen atom, an SO group or an $SO_2$ group,
Z denotes an alkylene group with 1 to 6 carbon atoms in the main chain, which can optionally be substituted,
R denotes an $NH_2$, $NHR^1$ or $NR^1R^2$ group,
in which
the substituents $R^1$ and $R^2$ are identical or different and denote an optionally substituted alkyl group, an optionally substituted phenyl group or an optionally substituted phenylalkyl group,
or in which
the radical $R^1$ in the group $NHR^1$ or $NR^1R^2$ is linked with a carbon atom of the substituent Z to form a 5-membered to 7-membered optionally substituted ring,
or in which
the radicals $R^1$ and $R^2$ together with the nitrogen atom to which they are attached form an optionally substituted azabicycloalkyl radical with 6 to 10 ring members,
or in which
R denotes a cycloalkyleneimino, cycloalkenylimino or cycloalkadienyleneimino group which has a total of 4 to 7 ring members and is optionally interrupted by O, S, NH or $NR^1$ and/or substituted by one or two alkyl groups, and
$R^3$ denotes an optionally substituted $C_1$ to $C_4$ alkyl group, or a $C_2$ to $C_6$ alkenyl group.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfoic, ethylenesulfonic, benzenesulfonic, halogenobenzenesulfonic, toluensulfonic, naphthalenesulfonic and sulfanilic acid; methionine; tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds according to the present invention have an excellent anthelmintic activity, in particular after oral and after parenteral administration.

Particularly preferred compounds of the present invention, are those in which
X denotes an oxygen or sulphur atom,
Z denotes a straight-chain or branched alkylene group with 1 to 6 carbon atoms, in the main chain,
R denotes an $NHR^1$ or $NR^1R^2$ group,
in which
$R^1$ and $R^2$ are identical or different and denote a $C_1$ to $C_6$ alkyl group,
or in which
the radical in the groups $NHR^1$ or $NR^1R^2$ is linked with a carbon atom of the alkylene group Z to form a 5-membered or 6-membered ring and the radical $R^2$ in the group $NR^1R^2$ denotes a $C_1$ to $C_6$ alkyl group,
or in which
the radicals $R^1$ and $R^2$ together with the nitrogen atom to which they are attached, form an azabicycloalkyl radical with 6 to 10 ring members, or in which
R denotes a cycloalkyleneimino group which has a total of 5 to 7 ring members and is optionally interrupted by oxygen, sulphur or an NH or $NR^1$ group and optionally substituted by one or two $C_1$ to $C_4$ alkyl groups, and in which $R^1$ denotes a $C_1$ to $C_4$ alkyl group and
$R^3$ denotes a $C_1$ to $C_4$ alkyl group.

According to the present invention there is further provided a process for the production of a compound of the invention in which (a) o-phenylene-diamine derivative of the general formula

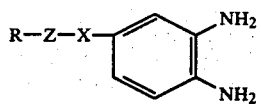
(II)

in which
R, X and Z have the above-mentioned meanings, is reacted with an acid derivative of the general formula

Y—COOR³ (III)

in which
$R^3$ has the above-mentioned meaning and
Y denotes one of the following radicals:

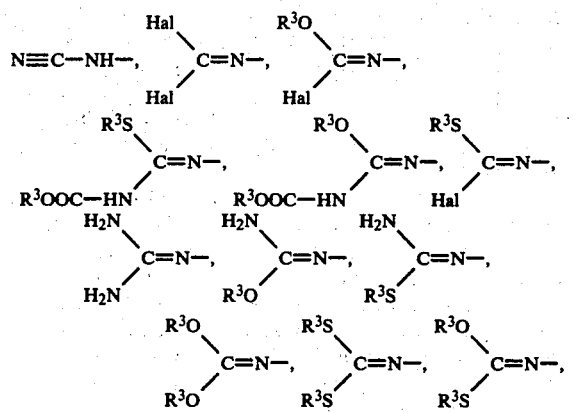

in which
$R^3$ has the above-mentioned meaning and
Hal denotes a halogen atom,
or (b) a 2-aminobenzimidazole derivative of the general formula

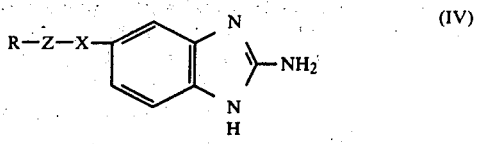
(IV)

in which
R, X and Z have the above-mentioned meanings, is reacted with a carbonic acid derivative of the general formula

(V)

in which
$R^3$ has the above-mentioned meaning and
A denotes a halogen atom, an optionally substituted alkoxy group or a radical of the formula OCOOR³,
$R^3$ has the above-mentioned meaning,
optionally in the presence of acid-binding agents, or (c) to obtain a compound of the formula (I) in which X denotes an SO group or an $SO_2$ group, thiobenzimidazolylcarbamic acid ester of the general formula

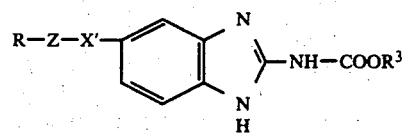
(VI)

in which
R and Z have the above-mentioned meaning and
X' denotes a sulphur atom,
is reacted with an oxidising agent; and thereafter isolating the end product obtained by reaction variant (a), (b), or (c).

Surprisingly, the benzimidazolylcarbamic acid esters of the present invention exhibit a pronounced anthelmintic action, even when they are administered in aqueous solution in the form of their water-soluble salts. Such administration is not possible with the known commercial products Parbendazole and Mebendazole. The substances according to the invention thus represent an advance in pharmacy.

The compounds according to the present invention can exist in tautomeric forms, as shown in the following general equation:

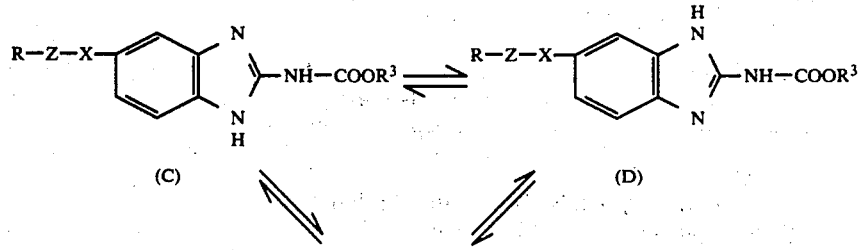

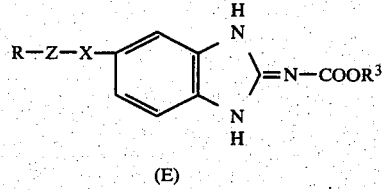

(E)

In these tautomeric formulae, the substitutent grouping R-Z-X is linked with the benzimidazole ring either in the 5-position (formulae C and E) or in the 6-position (formula D).

For reasons of uniformity, the particular structural formulae are in each case formulated herein in the same manner, namely according to formula C. From the point of view of nomenclature, the substituent grouping R-Z-X is thus also herein designated with the 5-position.

If 4-diethylamino-ethylthio-1,2-phenylenediamine and N-[(bis-chloro)-methylene]-carbamic acid methyl ester are used as starting substances in process variant (a), the course of the reaction can be represented by the following equation:

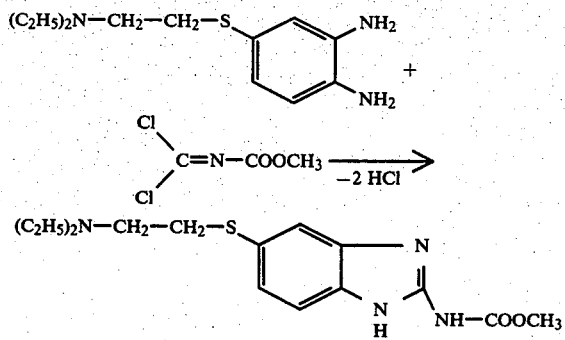

If 2-amino-5-(2-diethylaminoethylthio)-benzimidazole and chloroformic acid methyl ester are used as starting substances in process variant (b), the course of the reaction can be represented by the following equation:

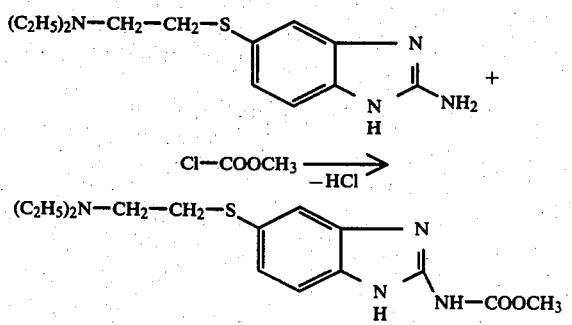

If 5-(2-diethylaminoethylthio)-benzimidazole-2-carbamic acid methyl ester and 1 equivalent of hydrogen peroxide are used as starting substances in process variant (c), the course of the reaction can be represented by the following equation:

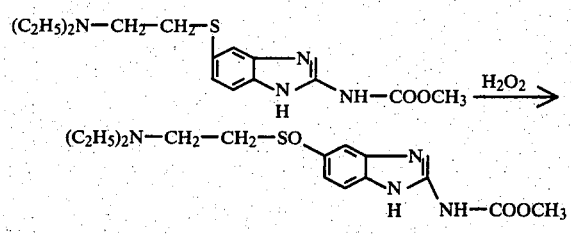

If 2 equvalents of hydrogen peroxide are used in process variant (c), the corresponding sulphonyl compound is formed:

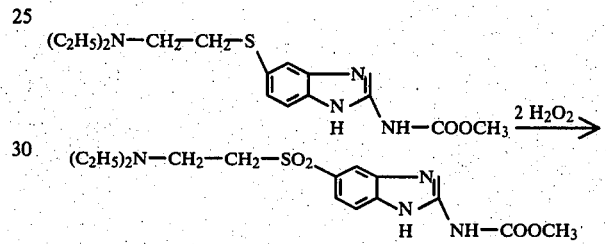

Optionally substituted alkylene groups Z with 1 to 6 carbon atoms in the main chain which may be mentioned are the following alkylene groups optionally substituted by $C_1$ to $C_4$ alkyl: $-CH_2-$, $-CH_2-CH_2-$, $-CH_2-CH_2-CH_2-$, $-(CH_2)_4-$,

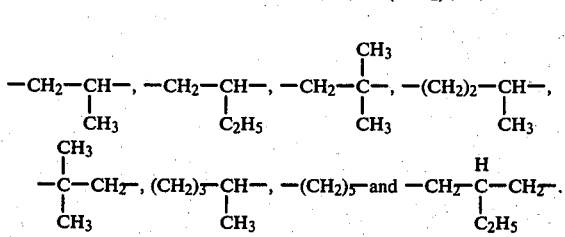

If $R^1$ or $R^2$ denotes an optionally substituted alkyl group, that group is preferably a $C_1$ to $C_6$ alkyl group and more preferably a $C_1$ to $C_4$ alkyl group, optionally substituted by halogen, cyano, $C_1$ to $C_4$ alkoxy or nitro. Examples which may be mentioned are: methyl, ethyl, n- and i-propyl and n-, i and t.-butyl.

Possible substituents for optionally substituted phenyl $R^1$ and $R^2$ are: $C_1$ to $C_4$ alkyl, $C_1$ to $C_4$ alkoxy, halogen, preferably fluorine, chlorine or bromine, trifluoromethyl, nitro and cyano. If $R^1$ or $R^2$ denotes an optionally substituted phenylalkyl group, that group is preferably a phenylalkyl group which is optionally substituted by $C_1$ to $C_4$ alkyl, $C_1$ to $C_4$ alkoxy, halogen, preferably fluorine, chlorine or bromine, trifluoromethyl, nitro and cyano the alkyl part of the phenylalkyl radical preferably having 1 to 4 carbon atoms. Examples which may be mentioned are: benzyl, β-phenylethyl, α-phenylethyl, 4-methylphenylmethyl, 3-methoxyphenylmethyl and 4-chlorophenylmethyl.

If $R^1$ of the groups $NHR^1$ or $NR^1R^2$ is linked with a carbon atom of the substituent Z to form a 5-membered to 7-membered optionally substituted ring, a heterocyclic ring system is thereby formed. Substituents of this heterocyclic system are preferably $C_1$ to $C_4$ alkyl groups.

Typical examples of such substituted heterocyclic radicals are: 1-methyl-3-pyrrolidyl, 1-methyl-3-piperidyl, 1-methyl-4-piperidyl, 1-methyl-3-hexahydroazepinyl and 1-methyl-4-hexahydroazepinyl.

Further examples of such heterocyclic rings are 2-methylene-pyrrolidine, 2-methyl-, 3-methyl-, 4-methyl- and 5-methyl-2-methylene-pyrrolidine, 2-methylene-1-methylpyrrolidine, 1,2-dimethyl-, 1,3-dimethyl-, 1,4-dimethyl- and 1,5-dimethyl-2-methylene-pyrrolidine, 2-ethyl-2-methylene-pyrrolidine, 2-(1-ethylene)-pyrrolidine, 2-(2-ethylene)-pyrrolidine, 2-(1-ethyl)-1-methyl-pyrrolidine, 2-(1-ethylene)-1-methylpyrrolidine, 2-methylene-piperidine, 2-methyl-2-methylene-piperidine, 2-(1-ethylene)-piperidine, 2-(2-ethylene)-piperidine, 2-(1-ethylene)-2-methyl-piperidine, 2-(2-ethylene)-2-methyl-piperidine, 1-methyl-2-methylenepiperidine, 2-methylene-hexahydroazepine, 2-methyl-2-methylene-hexahydroazepine and 1,2-dimethyl-2-methylenehexahydroazepine.

Optionally substituted azabicycloalkyl radicals $NR^1R^2$ with 6 to 10 ring members are preferably azabicycloalkyl radicals which are optionally substituted by $C_1$ to $C_4$ alkyl. The following radicals may be mentioned as examples: 2-azabicyclo[2.2.2]octyl, 3-azabicyclo[3.2.1]octyl, 2-methyl-3-azabicyclo[3.2.1]octyl, 2-ethyl-3-azabicyclo[3.2.1]octyl, 2,4-dimethyl-3-azabicyclo[3.2.1]octyl, 1,8,8-trimethyl-3-azabicyclo[3.2.1]octyl, 1,6,6-trimethyl-3-azabicyclo[3.2.1]octyl, 2,2,4,4-tertamethyl-3-azabicyclo[3.2.1]octyl, 2-azabicyclo[3.2.1]octyl, 6-azabicyclo[3.2.1]octyl, 8-azabicyclo[3.2.1]octyl, 3-azabicyclo[4.1.1]octyl, 3-azabicyclo[3.3.0]octyl, 3-azabicyclo[3.3.1]nonyl, 6-methyl-3-azabicyclo[3.3.1]nonyl, 9-azabicyclo[3.3.1]nonyl, 2-azabicyclo[3.3.1]nonyl, 2-azabicyclo[3.2.2]nonyl, 3-azabicyclo[3.2.2]nonyl, 9-azabicyclo[4.2.1]nonyl, 2-azabicyclo[4.3.0]nonyl, cis- and trans-8-azabicyclo[4.3.0]nonyl, 1,6-dimethyl-8-azabicyclo[4.3.0]nonyl, cis- and trans-7-azabicyclo[4.3.0]nonyl, 3-azabicyclo[3.2.0]heptyl, 2-methyl-3-azabuctcki[3.2.0]heptyl, 2-azabicyclo[2.2.1]heptyl, 7-azabicyclo[2.2.1]heptyl, 3-azabicyclo[3.1.1]heptyl, 6-azabicyclo[3.1.1]heptyl, 6-azabicyclo[3.3.1]heptyl, 3-azabicyclo[4.1.0]heptyl, 3-azabicyclo[3.1.0]hexyl, 1-methyl-3-azabicyclo[3.1.0]hexyl, 1,5-dimethyl-3-azabicyclo[3.1.0]hexyl and 3-azabicyclo[3.1.0]hexyl.

Possible cycloalkyleneimino, cycloalkenylimino or cycloalkadienyleneimino groups which have 4 to 7 ring members and are optionally interrupted by O, S, NH or $NR^1$ and/or substituted by one of two alkyl groups are preferably systems of this type which are optionally substituted by $C_1$ to $C_4$ alkyl. The following radicals may be mentioned as examples: pyrrolidino, 2-methyl-, 3-methyl-, 2,3-dimethyl-, 2,4-dimethyl- and 3,4-dimethylpyrrolidino, piperidino, 2-methyl-, 3-methyl-, 4-methyl-, 2,4-dimethyl-, 2,5-dimethyl-, 2,6-dimethyl-, 3,4-dimethyl-, and 4-ethyl-piperidino, 1,2,3,6-tetrahydropiperidino, 4-methyl-,3,4-dimethyl-, 4-ethyl-, 4-isopropyl- and 3,5-dimethyl-1,2,3,6-tetrahydro-piperidino, hexahydroazepino, 2-methyl-, 3-methyl- and 4-methylhexahydroazepino, morpholino, thiomorpholino, piperazino, N-methylpiperazino, N-ethyl-piperazino, 2-methyl-, 3-methyl and 3,5-dimethyl-piperazino, 2-methylmorpholino and 2,6-dimethylenemorpholino.

Examples of $R^3$ where $R^3$ denotes an optionally substituted $C_1$ to $C_4$ alkyl group are methyl, ethyl, n-propyl, i-propyl and n-, i- and t.-butyl, optionally substituted by $C_1$ to $C_4$ alkoxy, halogen (preferably fluorine, chlorine or bromine), trifluoromethyl, cyano or nitro.

Examples of $R^3$ where $R^3$ denotes a $C_2$ to $C_6$ alkenyl group are ethenyl, propen-1-yl, propen-2-yl and buten-3-yl.

Some of the o-phenylenediamine derivatives of the formula (II) to be employed according to the invention, as starting materials are novel. However, they can easily be prepared, as shown by the following example, by reacting optionally substituted amino-alkanols or-thiols, appropriately in the form of their alkali metal salts, with 5-chloro-2-nitroaniline and subsequently reducing the products with, for example, (Raney Ni/$H_2$); (Pd-C catalyst/$H_2$); or (PtO$_2$ catalyst/$H_2$), for example:

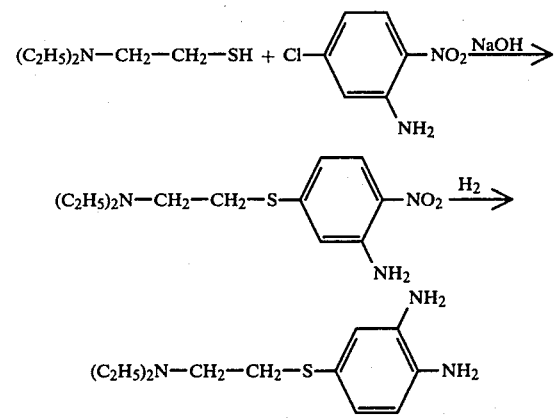

Other routes to the above-mentioned compounds of the formula (II) are also possible. Thus, 2-nitro-5-aminoalkyl-mercapto-anilides are oxidised with a oxidising agent to give 2-nitro-5-aminoalkyl-sulphinyl- or 2-nitro-5-aminoalkyl-sulphonyl-anilides, these products are subsequently saponified to give the corresponding anilines and the anilines are reduced to give substituted sulphinyl- or sulphonyl-2,2-phenylenediamines, as may be shown by the following examples:

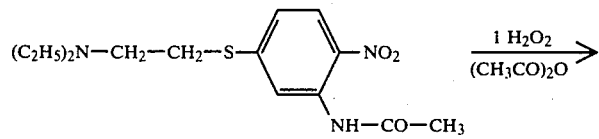

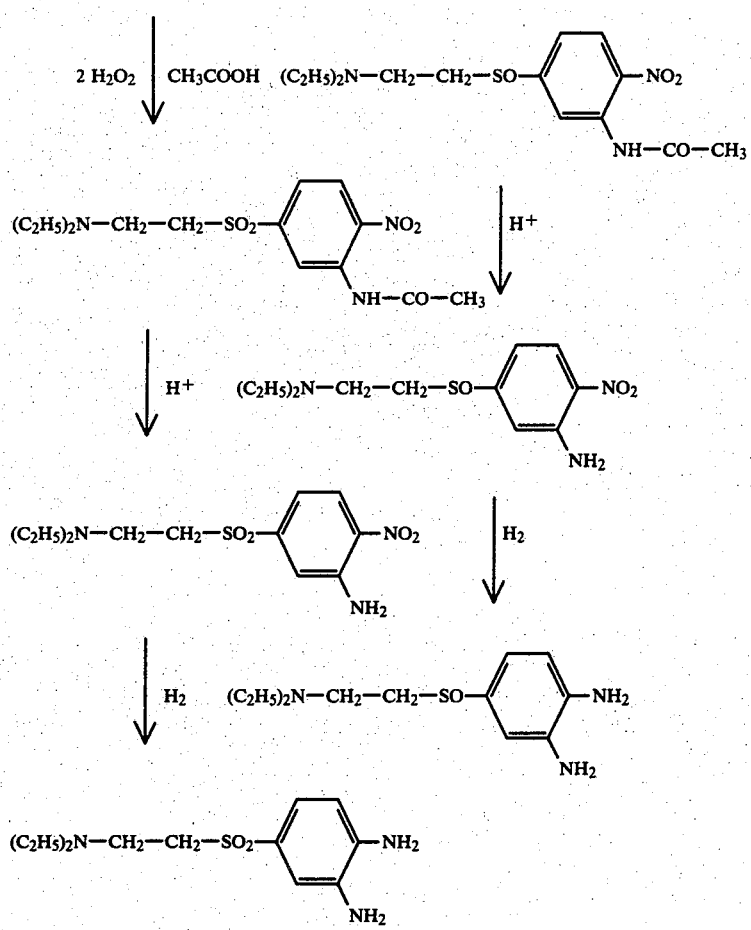

Most of the acid derivatives of the formula (III) employed as starting substances are known.

Examples of starting substances of the formula (III) which may be mentioned are: N-methoxycarbonyl-cyanamide, N-methoxycarbonylisothiourea methyl ether, N-methoxycarbonylisourea methyl esther, N-methoxycarbonylguanidine, N-[(bis-methoxy)methylene]-carbamic acid methyl ester, N-[(bis-methylmercapto)methylene]-carbamic acid methyl ester, N-methoxy-(methylmercapto)-methylene]-carbamic acid methyl ester and N,N'-bis-methoxycarbonyl-isothiourea S-methyl ether.

Starting compounds of the formula (III) which are not known can be prepared by processes which are in themselves known.

Some of the 2-aminobenzimidazole derivatives of the formula (IV) are novel, but they can easily be prepared by reacting phenylenediamine derivatives of the formula (II) and cyanogen chloride with one another in an inert solvent, if appropriate with the addition of a tertiary base, such as triethylamine, or in an aqueous/alcoholic solution with the addition of a base, such as, for example, NaHCO$_3$ or NaOH, for example

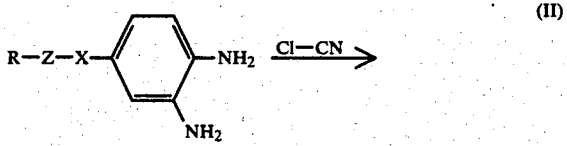

(II)

-continued

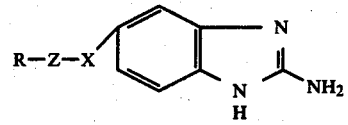

The substances according to the invention can be used in the free form of in the form of their physiologically acceptable salts with inorganic and organic acids, for example as hydrohalides, preferably hydrochlorides, sulphates, phosphates, nitrates, maleates, fumarates, acetates, methanesulphonates, hydroxyacetates, or naphthalene-disulphonates.

In carrying out process variant (a), of the acid derivatives of the formula (III), N-methoxycarbonylcyanamide, N-methoxycarbonylisothiourea alkyl ethers, N-methoxycarbonylisourea alkyl ethers, N,N'-bis-methoxycarbonyl-isothiourea S-methyl ether, N-methoxycarbonylguanidine, N-[(bisalkoxy)methylene]-carbamic acid esters, N-[(bisalkylmercapto)methylene]-carbamic acid esters and N-[alkoxy-(alkylmercapto)-methylene]-carbamic acid esters are preferably reacted with the phenylenediamine derivatives of the formula (II) at 0° to 150° C., more preferably at 30° to 120° C., preferably in a solvent, such as an alcohol (e.g. methanol, ethanol, propanol, isopropanol, etc), dilute acetic acid, ethylene glycol, tetrahydrofurane, dioxane, benzene, toluene or water. It is advantageous to carry out the reaction in solvents which contain water and in which a pH range of 2 to 7, preferably 2 to 5, is maintained by adding an organic acid, such as acetic acid, lactic acid or p-toluenesulphonic acid, or an alkali metal salt of an organic acid.

The N-[(bis-halogen)-methylene]-carbamic acid esters are advantageously subjected to condensation reactions with the phenylenediamine derivatives of the formula (II) in the presence of a base, such as trimethylamine, pyridine, sodium hydroxide solution, sodium bicarbonate or sodium carbonate, at 0° to 100° C., preferably 0° to 50° C.

The N-[alkoxy-(halogen)-methylene]-carbamic acid esters and N-[alkylmercapto-(halogen)-methylene]-carbamic acid esters are advantageously first reacted in he presence of an organic or inorgaic base, such as triethylamine, pyridine, sodium hydroxide solution or sodium carbonate, at room temperature and the products are then subjected to the condensation reaction at 0° to 150° C., preferably at 20°-120° C., by heating, preferably in a pH range from 2 to 5, by adding an organic acid, such as acetic acid or lactic acid.

In process variant (b), the reaction is preferably carried out at temperatures between 20° and 150° C., more preferably between 60° and 120° C., preferably in the presence of an organic base, such as triethylamine or pyridine, or an inorganic base, such as an alkali metal alcoholate of alkaline earth metal alcoholate, for example sodium methylate, or an alkali metal hydroxide or alkaline earth metal hydroxide, for example sodium hydroxide, in an organic solvent which is inert for this reaction, such as, for example, tetrahydrofurane, dioxane, benzene, toluene, chlorobenzene, acetonitrile, acetone, methyl ethyl ketone, diethylene glycol dimethyl ether, methanol and ethanol or mixtures of the above-mentioned diluents.

In reaction variant (c), it is preferred that 1 mol of the compound of formula (VI) is reacted with one or at least 1 mol of the oxidising agent under process conditions which are in themselves known, in an inert organic solvent or solvent mixture, for example in water, acetic acid, formic acid, acetic anhydride or propionic preferably at temperatures between about 0° and 100° C., more preferably between 0° and 80° C. Working up is effected by customary methods.

The oxidising agents employed as starting materials in process variant (c) are already known.

Examples which may be mentioned are: organic peracids, such as a $C_1$-$C_6$-per alkanoic acid, for example, peracetic acid, performic acid; perbenzoic acid; halo-substituted perbenzoic acid, for example, m-chloroperbenzoid acid or monoperphthalic acid, inorganic peroxides, such as hydrogen peroxide, dissolved in water or if appropriate dilute organic acids, inorganic oxidising agents, such as chromic acid, nitric acid, potassium permanganate, chlorine, bromine or halogen oxyacids, such as hypochlorous, chlorous, chloric or perchloric acid, tert.-butyl hypochlorite, methyl hypochlorite, tert.-butyl chromate, organic N-halogen compounds, such as N-chlorosuccinimide or N-bromosuccinimide, as well as N-halogenosulphonic acid amides of N-halogenocarboxylic acid amides.

By choosing the reaction conditions in a manner corresponding to that known from the literature, the oxidation potential can be adjusted accordingly and the reaction can be guided for the preparation of the sulphoxides or of the sulphones.

Active compounds according to the invention which may be mentioned are: 5-(2-diethylaminoethylthio)-benzimidazolyl-2-carbamic acid methyl ester, 5-(2-dimethylaminoethylthio)-benzimidazolyl-2-carbamic acid methyl ester, 5-(3-dimethylaminopropylthio)-benzimidazolyl-2-carbamic acid methyl ester, 5-(2-dimethylaminopropylthio)benzimidazolyl-2-carbamic acid methyl ester, 5-(2-morpholinoethylthio)-benzimidazolyl-2-carbamic acid methyl ester, 5-(2-morpholinopropylthio)-benzimidazolyl-2-carbamic acid methyl ester and the compounds of the general formula (I) listed in the Examples.

The compounds according to the invention have an excellent activity against helminthes, in particular a surprisingly good and broad action against the following nematodes and cestodes:

1. Hookworms (for example *Bunostomum trigonocephalum* and *Uncinaria stenocephala*);
2. Trichostrongylides (for example *Haemonchus contortus, Trichostrongylus colubriformis, Ostertagia circumcincta, Nippostrongylus muris* and *Cooperia curticei*);
3. Strongylides (for example *Oesophagostomum columbianum*);
4. Rhabditides (for example *Strongyloides ratti*);
5. Ascarides (for example *Toxocara canis, Toxascaris leonina* and *Ascaris suum*);
6. Thin worms (for example *Aspiculuris tetraptera*);
7. Heterakides (for example *Heterakis spumosa*);
8. Whip worms (for example *Trichuris muris*);
9. Filariae (for example *Litomosoides carinii* and *Dipetalonema witei*);
10. Tapeworms (for example *Taenia pisiformis* and *Hymenolepis nana*).

The action was examined in animal experiments after oral and parenteral administration to test animals heavily infested with parasites. The dosage used were tolerated very well by the test animals.

The new active compounds can be used as anthelmintic agents in medicine.

As stated above, the invention also relates to the use in medicine of the compounds of the invention.

The present invention provides pharmaceutical compositions containing as an active ingredient a compound of the invention in admixture with a solid, liquid or liquefied gaseous diluent.

The invention further provides pharmaceutical compositions containing as an active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agaragar, calcium carbonate and sodium bicarbonate; (e) agents for retarding dissolution e.g. paraffin; (f) resorption acceleratores, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g.water, ehtyl alcohol, propylene glycol, surface-active agents (e.g. ethoxylated isostearyl alcohols, polyoxyethylene sorbite and sorbitane esters), microcrystalline cellulose, aluminium-metahydroxide, bentonite, agar-agar and tragacanth or mixtures thereof.

All the pharmaceutical compostions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred dialy dose for administration of the medicaments of the invention is 50 to 5,000 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously) or rectally, preferably parenterally, in particular subcutaneously, or orally. Preferred pharmaceutical compositions and medicaments are therefore those adapted for administration such as parenteral or oral administration. Administration in the method of the invention is preferably parenteral or oral administration.

In general it has proved advantageous to administer amounts of from 1 mg to 100 mg/kg of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the production of compounds of the present invention.

EXAMPLE 1

5-(2-Diethylaminoethylthio)-benzimidazolyl-2-carbamic acid methyl ester 10 ml of triethylamine and 5.6 g (0.031 mol) of N-[(bis-chloro)-methylene]-carbamic acid methyl ester are added dropwise to 7.1 g (0.03 mol) of 4-(2-diethylaminoethylthio)-1,2-phenylenediamine, dissolved in 100 ml of chloroform, at 20° C. The mixture is heated under reflux for 30 minutes. After distilling off the solvent in vacuo, the residue is triturated with water several times, filtered off, triturated again thoroughly with n-hexane and filtered off again. Yield: 7.9 g of 5-(2-diethylaminoethylthio)-benzimidazolyl-2-carbamic acid methyl ester.

Melting point: 162°-164° C. (decomposition), hydrochloride melting point: 200°-201° C. (decomposition).

The 4-(2-diethylaminoethylthio)-1,2-phenylenediamine, oil, used as the starting material is obtained by catalytic hydrogenation of 2-nitro-5-(2-diethylaminoethylthio)-aniline.

The 2-nitro-5-(2-diethylaminoethylthio)-aniline (melting point: 42°-44° C.) is in turn prepared by reacting 2-diethylaminoethanethiol with 5-chloro-2-nitroaniline in the presence of sodium methylate in alcohol.

EXAMPLE 2

N-Methoxycarbonyl-isothiourea methyl ether, which has been obtained by reacting 7.8 g of S-methylisothiourea sulphate with 4.5 g of chloroformic acid methyl ester and 17 g of 25% strength sodium hydroxide solution, is brought to pH 5 with acetic acid ($\sim$5-6 ml). 7.1 g of 4-(2-diethylaminoethylthio)-1,2-phenylenediamine, dissolved in alcohol and 3 ml of acetic acid, are added, the mixture is heated to 80°-85° C. for 1 hour and cooled, the reaction product is filtered off and, after washing with water and alcohol, 9 g of 5-(2-diethylaminoethylthio)-benzimidazolylcarbamic acid methyl ester of melting point 162°-164° C. are obtained.

The same compound is obtained analogously, by condensation with N-methoxycarbonyl-isourea methyl ether in an amount of 4.2 g, or by condensation of 4-(2-diethylaminoethylthio)-1,2-phenylenediamine (0.03 mol) with 0.03 mol of N-[(bis-ethoxy)-methylene]-carbamic acid methyl ester at 110° to 140° C. in glycol (yield: 5.2 g) or with 0.03 mol of N-[(bis-alkylmercapto)-methylene]-carbamic acid methyl ester (yield: 4.9 g) or with 0.03 mol of N-[ethoxy-(methylmercapto)-methylene]-carbamic acid methyl ester (yield: 4.1 g) or with 0.03 mol of N-methoxycarbonylguanidine at 140° to 160° C. (yield: 3.9 g) or with 0.03 mol of methoxycarbonylcyanamide in water at 80° to 100° C., a pH of 2 to 4 being established with hydrochloric acid (yield: 3.8 g), or with 0.03 mol of N,N'-bis-methoxycarbonyl-isothiourea S-methyl ether (yield: 8.3 g).

EXAMPLE 3

16.7 g (0.1 mol) of N-[chloro-(methylmercapto)methylene]-carbamic acid methyl ester, dissolved in a little chloroform, are added dropwise to 24.8 g (0.1 mol) of 4-(2-diethylaminoethylthio)-1,2-phenylenediamine and 10.1 g (0.1 mol) of triethylamine in 300 ml of dlry chloroform at 0° C., whilst stirring. The mixture is subsequently stirred at 25° to 30° C. for 2 to 3 hours and evaporated in vacuo, 200 ml of alcohol, 10 ml of water and 0.5 g of p-toluenesulphonic acid are added and the mixture is heated to 90° C. for 2 hours. After evaporation, the residue is stirred with water and filtered off and the reaction product is washed with alcohol. Yield: 26.2 g of 5-(2-diethylaminoethylthio)-benzimidazolyl-2-carbamic acid methyl ester. If 0.1 mol of N-[chloro-(methoxy)methylene]-carbamic acid methyl ester is subjected to an analogous condensation reaction with 4-(2-diethylaminoethylthio)-1,2-phenylenediamine, a yield lof 18.5 g is obtained.

EXAMPLE 4

27.3 g (0.1 mol) of 2-amino-5-(2-diethylaminoethylthio)-benzimidazole are added to a solution of 2.4 g of sodium in 200 ml of methanol, 5.6 g of carbonic acid dimethyl ester are added dropwise and the mixture is heated under reflux for one hour. It is evaporated in vacuo, the residue is washed successively with water, dilute acetic acid and alcohol and, after drying, 21.4 g of 5-(2-diethylaminoethylthio)-benzimidazolyl-2-carbamic acid methyl ester are obtained, melting point 162°-164° C.

The same compound is formed by reacting 2-amino-5-(2-diethylaminoethylthio)-benzimidazole with an equivalent amount of pyrocarbonic acid dimethyl ester in chloroform at 40° C.

The same compound is likewise formed by reacting 0.1 mol of 2-amino-5-(2-diethylaminoethylthio)-benzimidazole, dissolved in chloroform, with 0.1 mol of chloroformic acid methyl ester in the presence of 0.1 mol of triethylamine. When the dropwise addition was ended, the mixture is heated under reflux for a further 5 to 6 hours. Yield: 22.6 g.

The 2-amino-5-(2-diethylaminoethylthio)-benzimidazole used as the starting material is formed by reacting 4-(2-diethylaminoethylthio)-1,2-phenylenediamine with cyanogen chloride or bromide in tetrahydrofurane, alcohol or water.

EXAMPLE 5

7.2 g of 5-(2-diethylaminoethylsulphinyl)-benzimidazolylcarbamic acid methyl ester are obtained from 7.1 g of 4-(2-diethylaminoethylsulphinyl)-1,2-phenylenediamine and 5.6 g of N-[(bis-chloro)-methylene]-carbamic acid methyl ester by the preparation described in Example 1.

The 4-(2-diethylaminoethylsulphinyl)-1,2-phenylenediamine used as the starting material is obtained by the following route: 2-nitro-5-(2-diethylaminoethylthio)propionanilide is oxidised, in acetic anhydride, with one equivalent of $H_2O_2$ to give 2-nitro-5-(2-diethylaminoethylsulphinyl)-propionanilide, this compound is subsequently saponified to give 2-nitro-5-(2-diethylaminoethylsulphinyl)aniline and the aniline is reduced catalytically to give 5-(2-diethylaminoethylsulphinyl)-1,2-phenylenediamine.

EXAMPLE 6

12.8 g of 5-(2-diethylaminoethylthio)-benzimidazole-2-carbamic acid methyl ester are dissolved in 500 ml of acetic anhydride. 4.7 g of 30% strength hydrogen superoxide solution are added dropwise to this solution and the mixture is subsequently stirred for 3 hours and evaporated in vacuo. The residue is triturated with a mixture of petroleum ether/ethyl acetate. After filtering off the product, 5-(2-diethylaminoethylsulphinyl)benzimidazolyl-2-carbamic acid methyl ester is obtained.

6 g of 5-(2-diethylaminoethylsulphonyl)-benzimidazol-yl-2-carbamic acid methyl ester are obtained from 12.8 g of 5-(2-diethylaminoethylthio)-benzimidazolyl-2-carbamic acid methyl ester, dissolved in 250 ml of acetic acid, with 12 g of 30% strength hydrogen peroxide by a corresponding procedure.

EXAMPLES 7 to 159

The following benzimidazolyl-2-carbamic acid esters are obtained from substituted phenylenediamine derivatives by the method described in Example 1:

| | Starting substances | | | Compounds prepared according to the invention | | |
|---|---|---|---|---|---|---|
| No. | Melting point °C. | Boiling point °C. (mm Hg) | $R^4$ | | $R^3$ | Melting point °C. | Salt melting point °C. |
| 7 | 66–68 | 178–183 (0.1) | $(CH_3)_2N-CH_2-CH_2-S$ | | $CH_3$ | 185–186 (decomposition) | HCl 155–156 (decomposition) |
| 8 | 68–70 | 190–195 (0.2) | $(CH_3)_2N-CH_2-CH_2-CH_2-S$ | | $CH_3$ | 184–185 (decomposition) | HCl 160–162 (decomposition) |
| 9 | 66–68 | 190–200 (0.1) | $(C_2H_5)_2N-CH_2-CH_2-CH_2-S$ | | $CH_3$ | 155–156 (decomposition) | |
| 10 | 104–105 | 185–190 (0.1) | pyrrolidinyl$-CH_2-CH_2-S$ | | $CH_3$ | 186–187 (decomposition) | HCl 171–172 (decomposition) 2HCl 182–183 |
| 11 | Oil | 190–200 (0.1) | pyrrolidinyl$-CH_2-CH(CH_3)-S$ | | $CH_3$ | 193–195 (decomposition) | HCl 198–200 (decomposition) |
| 12 | 115–116 | 195–200 (0.1) | piperidinyl$-CH_2-CH_2-S$ | | $CH_3$ | 208–210 (decomposition) | . 2HCl . 2H₂O, (decomposition) 110–112 |
| 13 | 150–152 | 195–200 (0.1) | morpholinyl$-CH_2-CH_2-S$ | | $CH_3$ | 175–176 (decomposition) | |
| 14 | 93–95 | 190–200 (0.1) | morpholinyl$-CH_2-CH(CH_3)-S$ | | $CH_3$ | 180–182 (decomposition) | |
| 15 | 87–90 | 200–210 (0.1) | $CH_3-N$(piperazinyl)$N-CH_2-CH_2-S$ | | $CH_3$ | 165–166 (decomposition) | |
| 16 | Oil | 200–210 (0.1) | $CH_3-N$(piperazinyl)$N-CH_2-CH(CH_3)-S$ | | $CH_3$ | 158–160 (decomposition) | |
| 17 | 72 | 190–195 (0.1) | $C_4H_9-NH-CH_2-CH_2-S$ | | $CH_3$ | 156 (decomposition) | HCl 175–176 (decomposition) |
| 18 | Oil | 200–205 (0.1) | piperidinyl$-CH_2-CH(CH_3)-S$ | | $CH_3$ | 181–183 (decomposition) | |
| 19 | | | $(CH_3)_2N-CH_2-CH(CH_3)-CH_2-S$ | | $CH_3$ | | |
| 20 | | | $(CH_3)_2N-C(CH_3)_2-CH_2-S$ | | $CH_3$ | | |
| 21 | | | $(CH_3)_2N-(CH_2)_4-S$ | | $CH_3$ | | |
| 22 | | 176–180 (0.2) | $(CH_3)_2N-CH_2-CH(CH_3)-S$ | | $CH_3$ | 171–172 (decomposition) | |
| 23 | | | $(CH_3)_2N-(CH_2)_5-S$ | | $CH_3$ | | |
| 24 | | | $(CH_3)_2N-CH(CH_3)-CH_2-S$ | | $CH_3$ | | |
| 25 | | | $(CH_3)_2N-CH(CH_3)-CH_2-CH_2-S$ | | $CH_3$ | | |
| 26 | | | $(CH_3)_2N-CH_2-C(CH_3)_2-CH_2-S$ | | $CH_3$ | | |
| 27 | | | $(CH_3)_2N-CH_2CH_2CH(CH_3)-S$ | | $CH_3$ | | |
| 28 | | | $(CH_3)_2N-CH_2-CH(CH_3)-CH_2-S$ | | $CH_3$ | | |
| 29 | | | $(C_2H_5)_2N-(CH_2)_4-S$ | | $CH_3$ | | |
| 30 | | | $(C_2H_5)_2N-(CH_2)_5-S$ | | $CH_3$ | | |
| 31 | oil | 180–190 (0.1) | $(C_2H_5)_2N-CH_2-CH(CH_3)-S$ | | $CH_3$ | 175 (decomposition) | |
| 32 | | | $(C_2H_5)_2N-C(CH_3)_2-CH_2-S$ | | $CH_3$ | | |
| 33 | | | $(C_2H_5)_2N-CH(CH_3)-CH_2-S$ | | $CH_3$ | | |

-continued

| | Starting substances | | Compounds prepared according to the invention | | | |
|---|---|---|---|---|---|---|
| No. | Melting point °C. | Boiling point °C. (mm Hg) | $R^4$ | $R^3$ | Melting point °C. | Salt melting point °C. |
| 34 | | | $(C_2H_5)_2N-CH(CH_3)-CH_2-CH_2-S$ | $CH_3$ | | |
| 35 | | | $(C_2H_5)_2N-CH_2-CH(CH_3)-CH_2-S$ | $CH_3$ | | |
| 36 | Oil | 195–200 (0.1) | $(C_2H_5)_2N-(CH_2)_3-CH(CH_3)-S$ | $CH_3$ | 180 (decomposition) | |
| 37 | | | $(C_3H_7)_2N-(CH_2)_2-S$ | $CH_3$ | | |
| 38 | | | $(CH_3)_2CHN-(CH_2)_2-S$ | $CH_3$ | | |
| 39 | 167–168 | 180–184 (0,05) | $(C_3H_7)_2N-CH_2-CH(CH_3)-S$ | $CH_3$ | 184–185 | |
| 40 | | | $(C_4H_9)_2N-(CH_2)_2-S$ | $CH_3$ | | |
| 41 | Oil | 190–200 (0,1) | $(C_4H_9)_2N-CH_2-CH(CH_3)-S$ | $CH_3$ | 184–186 (decomposition) | |
| 42 | | | $CH_3(C_2H_5)N-(CH_3)_2-S$ | $CH_3$ | | |
| 43 | | | $CH_3(C_2H_5)N-(CH_2)_3-S$ | $CH_3$ | | |
| 44 | | | $C_6H_5CH_2(CH_3)N-(CH_2)_2-S$ | $CH_3$ | | |
| 45 | Oil | Oil | $C_6H_5CH_2(CH_3)N-CH_2-CH(CH_3)-S$ | $CH_3$ | 159–161 (decomposition) | |
| 46 | | | $C_6H_5(CH_3)N-(CH_2)_2-S$ | $CH_3$ | | |
| 47 | | | $C_6H_5(CH_3)N-(CH_2)_3-S$ | $CH_3$ | | |
| 48 | | | 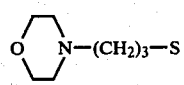 $O\!\!\diagup\!\!\diagdown N-(CH_2)_3-S$ | $CH_3$ | | |
| 49 | 86 | Oil | 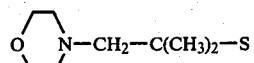 $O\!\!\diagup\!\!\diagdown N-CH_2-C(CH_3)_2-S$ | $CH_3$ | 224–226 (decomposition) | |
| 50 | | | 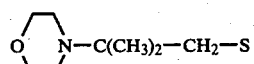 $O\!\!\diagup\!\!\diagdown N-C(CH_3)_2-CH_2-S$ | $CH_3$ | | |
| 51 | | | 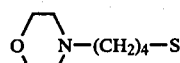 $O\!\!\diagup\!\!\diagdown N-(CH_2)_4-S$ | $CH_3$ | | |
| 52 | | | 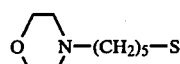 $O\!\!\diagup\!\!\diagdown N-(CH_2)_5-S$ | $CH_3$ | | |
| 53 | | |  $O\!\!\diagup\!\!\diagdown N-CH(CH_3)-CH_2-S$ | $CH_3$ | | |
| 54 | | | 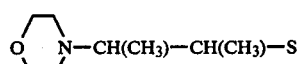 $O\!\!\diagup\!\!\diagdown N-CH(CH_3)-CH(CH_3)-S$ | $CH_3$ | | |
| 55 | | | 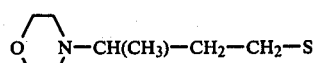 $O\!\!\diagup\!\!\diagdown N-CH(CH_3)-CH_2-CH_2-S$ | $CH_3$ | | |
| 56 | oil | oil | 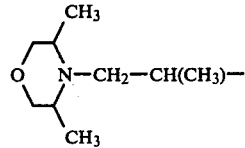 $\text{CH}_3$-substituted morpholinyl $N-CH_2-CH(CH_3)-S$ (with $CH_3$ groups) | $CH_3$ | 176 (decomposition) | |
| 57 | | | 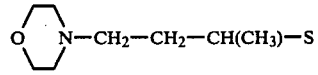 $O\!\!\diagup\!\!\diagdown N-CH_2-CH_2-CH(CH_3)-S$ | $CH_3$ | | |
| 58 | | | 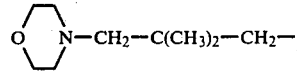 $O\!\!\diagup\!\!\diagdown N-CH_2-C(CH_3)_2-CH_2-S$ | $CH_3$ | | |
| 59 | | | 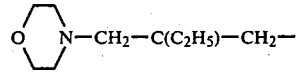 $O\!\!\diagup\!\!\diagdown N-CH_2-C(C_2H_5)-CH_2-S$ | $CH_3$ | | |

-continued
| | Starting substances | | Compounds prepared according to the invention | | | |
|---|---|---|---|---|---|---|
| No. | Melting point °C. | Boiling point °C. (mm Hg) | R⁴ | R³ | Melting point °C. | Salt melting point °C. |
| 60 | | | 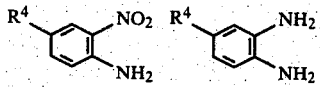 | $CH_3$ | | |
| 61 | | |  | $CH_3$ | | |
| 62 | | | 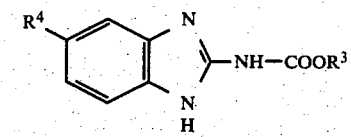 | $CH_3$ | | |
| 63 | | | 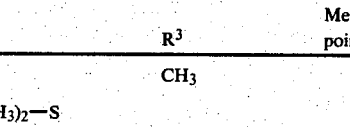 | $CH_3$ | | |
| 64 | | | 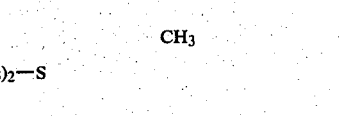 | $CH_3$ | | |
| 65 | | | 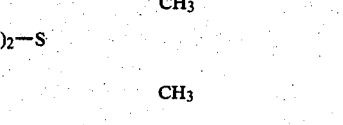 | $CH_3$ | | |
| 66 | | | 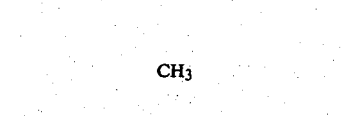 | $CH_3$ | | |
| 67 | | | 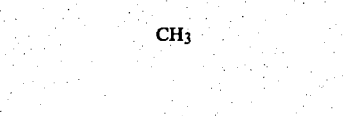 | $CH_3$ | | |
| 68 | | | 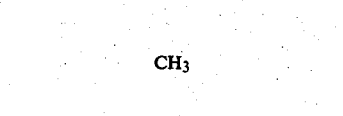 | $CH_3$ | | |
| 69 | | | 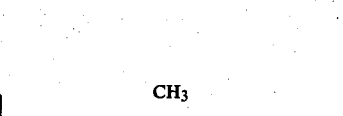 | $CH_3$ | | |
| 70 | | | 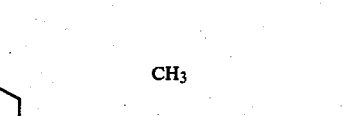 | $CH_3$ | | |
| 71 | | | 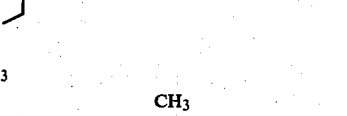 | $CH_3$ | | |
| 72 | | |  | $CH_3$ | | |

-continued
| | Starting substances | | Compounds prepared according to the invention | | | |
|---|---|---|---|---|---|---|
| No. | Melting point °C. | Boiling point °C. (mm Hg) | R⁴ | R³ | Melting point °C. | Salt melting point °C. |
| 73 | | | 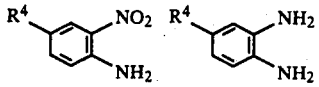 | CH₃ | | |
| 74 | | | 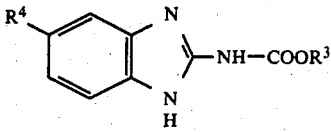 | CH₃ | | |
| 75 | | | 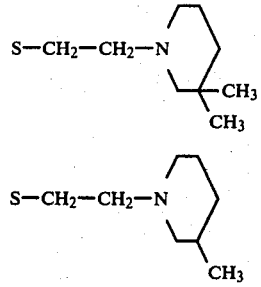 | CH₃ | | |
| 76 | | | 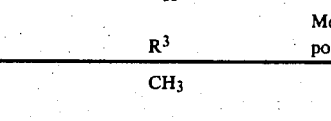 | CH₃ | | |
| 77 | | | 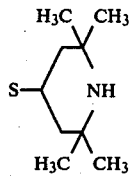 | CH₃ | | |
| 78 | | | S—CH₂CH₂N(CH₃)CH₂CH₂C₆H₅ | CH₃ | | |
| 79 | | | S—CH₂—CH₂—N(CH₃)C₆H₅ | CH₃ | | |
| 80 | | | 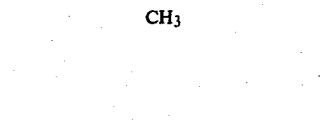 | CH₃ | | |
| 81 | | | 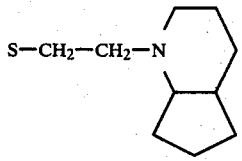 | CH₃ | | |
| 82 | | | 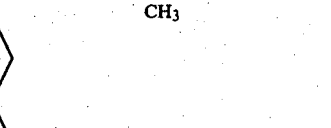 | CH₃ | | |
| 83 | | | 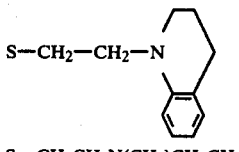 | CH₃ | | |
| 84 | | | 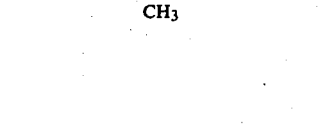 | CH₃ | | |

4,287,199

-continued

| | Starting substances | | Compounds prepared according to the invention | | | |
|---|---|---|---|---|---|---|
| | $R^4$-C$_6$H$_3$(NO$_2$)(NH$_2$) | $R^4$-C$_6$H$_3$(NH$_2$)$_2$ | $R^4$-benzimidazole-NH-COOR$^3$ | | | |
| No. | Melting point °C. | Boiling point °C. (mm Hg) | $R^4$ | $R^3$ | Melting point °C. | Salt melting point °C. |
| 85 | | | S—CH$_2$—CH$_2$—N(pyrrolidine with gem-diCH$_3$) | CH$_3$ | | |
| 86 | | | S—CH$_2$—CH$_2$—N(fused cyclobutane pyrrolidine) | CH$_3$ | | |
| 87 | | | C$_6$H$_5$NH—(CH$_2$)$_2$—S | CH$_3$ | | |
| 88 | | | C$_6$H$_5$NH—(CH$_2$)$_3$—S | CH$_3$ | | |
| 89 | | | C$_2$H$_5$NH—(CH$_2$)$_2$—S | CH$_3$ | | |
| 90 | | | C$_2$H$_5$NH—(CH$_2$)$_3$—S | CH$_3$ | | |
| 91 | | | C$_3$H$_7$NH—(CH$_2$)$_2$—S | CH$_3$ | | |
| 92 | | | (CH$_3$)$_2$CH—NH—(CH$_2$)$_2$—S | CH$_3$ | | |
| 93 | | | (CH$_3$)$_2$CH—NH—(CH$_2$)$_3$—S | CH$_3$ | | |
| 94 | | | (CH$_3$)$_2$CH—CH$_2$—NH—(CH$_2$)$_2$—S | CH$_3$ | | |
| 95 | Oil | Oil | C$_6$H$_{11}$(H)N—CH$_3$—CH(CH$_3$)—S | CH$_3$ | | 183 (decomposition) |
| 96 | | | (CH$_3$)$_2$CH—(CH$_2$)$_2$—NH—(CH$_2$)$_2$—S | CH$_3$ | | |
| 97 | | | (CH$_3$)$_3$C—NH—(CH$_2$)$_2$—S | CH$_3$ | | |
| 98 | 84 | Oil | (CH$_3$)$_3$C—NH—CH$_2$—C(CH$_3$)—S | CH$_3$ | | 186–188 (decomposition) |
| 99 | | | (CH$_3$)$_2$CH(CH$_2$)$_2$—NH—(CH$_2$)$_2$—S | CH$_3$ | | |
| 100 | | | S—CH$_2$—CH$_2$—N(tetrahydropyridine-3,4-diCH$_3$) | CH$_3$ | | |
| 101 | | | S—CH$_2$—CH$_2$—N(piperidine-3,5-diCH$_3$) | CH$_3$ | | |
| 102 | | | S—CH$_2$—CH$_2$—N(tetrahydropyridine-3-CH$_3$) | CH$_3$ | | |
| 103 | | | S—CH$_2$—CH$_2$—N(tetrahydropyridine-3-C$_2$H$_5$) | CH$_3$ | | |
| 104 | | | S—CH$_2$—CH$_2$—N(piperidine-CH$_2$C$_6$H$_5$) | CH$_3$ | | |
| 105 | | | S—CH$_2$—CH$_2$—N(bicyclic) | CH$_3$ | | |
| 106 | | | S—CH$_2$—CH$_2$—N(bicyclic) | CH$_3$ | | |
| 107 | | | S—CH$_2$—CH$_2$—N(bicyclic) | CH$_3$ | | |

-continued

| | Starting substances | | Compounds prepared according to the invention | | | |
|---|---|---|---|---|---|---|
| No. | Melting point °C. | Boiling point °C. (mm Hg) | R⁴ | R³ | Melting point °C. | Salt melting point °C. |
| 108 | | | S—CH₂—CH₂—N⟨bicyclic⟩ | CH₃ | | |
| 109 | | | S—CH₂—CH₂—N⟨bicyclic⟩ | CH₃ | | |
| 110 | | | (CH₃)₂N—CH₂—CH₂—S | C₂H₅ | | |
| 111 | | | (CH₃)₂N—CH₂—CH₂—CH₂—S | C₃H₇ | | |
| 112 | | | (C₂H₅)₂N—CH₂—CH₂—CH₂—S | C₂H₅ | | |
| 113 | | | ⟨pyrrolidinyl⟩N—CH₂—CH₂—S | C₄H₉ | | |
| 114 | | | ⟨pyrrolidinyl⟩N—CH₂—CH(CH₃)—S | C₂H₅ | | |
| 115 | | | ⟨piperidinyl⟩N—CH₂—CH₂—S | CH₂—CH=CH₂ | | |
| 116 | | | O⟨morpholinyl⟩N—CH₂—CH₂—S | CH₂—CH=CH₂ | | |
| 117 | | | O⟨morpholinyl⟩N—CH₂—CH(CH₃)—S | C₂H₅ | | |
| 118 | | | CH₃—N⟨piperazinyl⟩N—CH₂—CH₂—S | C₂H₅ | | |
| 119 | | | CH₃—N⟨piperazinyl⟩N—CH₂—CH(CH₃)—S | C₂H₅ | | |
| 120 | | | C₄H₉—NH—CH₂—CH₂—S | C₂H₅ | | |
| 121 | | | ⟨piperidinyl⟩N—CH₂—CH(CH₃)—S | C₂H₅ | | |
| 122 | | | (CH₃)₂N—CH₂—CH₂—O | CH₃ | | |
| 123 | | | (CH₃)₂N—CH₂—CH₂—CH₂—O | CH₃ | | |
| 124 | | | (C₂H₅)₂N—CH₂—CH₂—CH₂—O | CH₃ | | |
| 125 | | | ⟨pyrrolidinyl⟩N—CH₂—CH₂—O | CH₃ | | |
| 126 | | | ⟨pyrrolidinyl⟩N—CH₂—CH(CH₃)—O | CH₃ | | |
| 127 | | | ⟨piperidinyl⟩N—CH₂—CH₂—O | CH₃ | | |
| 128 | 107–109 | 185–195 (0.2) | O⟨morpholinyl⟩N—CH₂—CH₂—O | CH₃ | | 204–205 (decomposition) |
| 129 | 93–94 | oil | O⟨morpholinyl⟩N—CH₂—CH(CH₃)—O | CH₃ | | 118 (decomposition) |

-continued

| | Starting substances | | Compounds prepared according to the invention | | | |
|---|---|---|---|---|---|---|
| | $R^4$-C$_6$H$_3$(NO$_2$)(NH$_2$) | $R^4$-C$_6$H$_3$(NH$_2$)$_2$ | $R^4$-benzimidazole-NH-COOR$^3$ | | | |
| No. | Melting point °C. | Boiling point °C. (mm Hg) | $R^4$ | $R^3$ | Melting point °C. | Salt melting point °C. |
| 130 | 117 | Oil | C$_6$H$_5$(CH$_3$)N—CH$_2$—CH$_2$—O | CH$_3$ | 222 (decomposition) | |
| 131 | | | C$_6$H$_5$NH—CH$_2$—CH$_2$—O | CH$_3$ | | |
| 132 | | | CH$_3$—N(piperazine)N—CH$_2$—CH$_2$—O | CH$_3$ | | |
| 133 | 65–67 | 170–180 (0.2) | (C$_2$H$_5$)N—CH$_2$—CH$_2$—O | CH$_3$ | 190–191 (decomposition) | |
| 134 | 80–81 | oil | C$_4$H$_9$—NH—CH$_2$—CH$_2$—O | CH$_3$ | 130–131 (decomposition) | |
| 135 | | | piperidine-N—CH$_2$—CH(CH$_3$)—O | CH$_3$ | | |
| 136 | | | (CH$_3$)$_2$N—CH$_2$—CH$_2$—SO | CH$_3$ | | |
| 137 | | | (CH$_3$)$_2$N—CH$_2$—CH$_2$—CH$_2$—SO | CH$_3$ | | |
| 138 | | | (C$_2$H$_5$)$_2$N—CH$_2$—CH$_2$—CH$_2$—SO | CH$_3$ | | |
| 139 | | | pyrrolidine-N—CH$_2$—CH$_2$—SO | CH$_3$ | | |
| 140 | | | pyrrolidine-N—CH$_2$—CH(CH$_3$)—SO | CH$_3$ | | |
| 141 | | | piperidine-N—CH$_2$—CH$_2$—SO | CH$_3$ | | |
| 142 | | | morpholine-N—CH$_2$—CH$_2$—SO | CH$_3$ | | |
| 143 | | | morpholine-N—CH$_2$—CH(CH$_3$)—SO | CH$_3$ | | |
| 144 | | | CH$_3$—N(piperazine)N—CH$_2$—CH$_2$—SO | CH$_3$ | | |
| 145 | | | CH$_3$—N(piperazine)N—CH$_2$—CH(CH$_3$)—SO | CH$_3$ | | |
| 146 | | | C$_4$H$_9$—NH—CH$_2$—CH$_2$—SO | CH$_3$ | | |
| 147 | | | piperidine-N—CH$_2$—CH(CH$_3$)—SO | CH$_3$ | | |
| 148 | | | (CH$_3$)$_2$N—CH$_2$—CH$_2$—SO$_2$ | CH$_3$ | | |
| 149 | | | (CH$_3$)$_2$N—CH$_2$—CH$_2$—CH$_2$—SO$_2$ | CH$_3$ | | |
| 150 | | | (C$_2$H$_5$)$_2$N—CH$_2$—CH$_2$—CH$_2$—SO$_2$ | CH$_3$ | | |
| 151 | | | pyrrolidine-N—CH$_2$—CH$_2$—SO$_2$ | CH$_3$ | | |
| 152 | | | pyrrolidine-N—CH$_2$—CH(CH$_3$)—SO$_2$ | CH$_3$ | | |

-continued

| No. | Melting point °C. | Boiling point °C. (mm Hg) | R⁴ | R³ | Melting point °C. | Salt melting point °C. |
|---|---|---|---|---|---|---|
| 153 | | | (cyclohexyl)N—CH$_2$—CH$_2$—SO$_2$ | CH$_3$ | | |
| 154 | | | O(morpholino)N—CH$_2$—CH$_2$—SO$_2$ | CH$_3$ | | |
| 155 | | | O(morpholino)N—CH$_2$—CH(CH$_3$)—SO$_2$ | CH$_3$ | | |
| 156 | | | CH$_3$—N(piperazino)N—CH$_2$—CH$_2$—SO$_2$ | CH$_3$ | | |
| 157 | | | CH$_3$—N(piperazino)N—CH$_2$—CH(CH$_3$)—SO$_2$ | CH$_3$ | | |
| 158 | | | C$_4$H$_9$—NH—CH$_2$—CH$_2$—SO$_2$ | CH$_3$ | | |
| 159 | | | (cyclohexyl)N—CH$_2$—CH(CH$_3$)—SO$_2$ | CH$_3$ | | |

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to a warm-blooded animal is converted in the patient's body to the active compound.

We claim:

1. A 2-benzimidazolylcarbamic ester of the formula

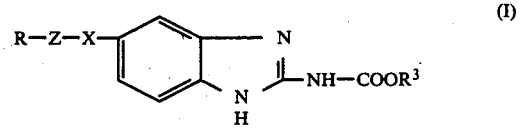

(I)

or a salt thereof in which

X denotes a sulphur atom, an oxygen atom, an SO group or an SO$_2$ group,

Z denotes an alkylene group with 1 to 6 carbon atoms in the main chain, which is unsubstituted or C$_1$–C$_4$-alkyl substituted, R denotes an NH$_2$, NHR$^1$ or NR$^1$R$^2$ group, in which the substituents R$^1$ and R$^2$ are identical or different and denote a C$_1$–C$_6$-alkyl group which is unsubstituted or substituted by halogen, cyano, C$_1$–C$_4$-alkoxy or nitro, a phenyl group which is unsubstituted or substituted by C$_1$–C$_4$-alkyl, C$_1$–C$_4$-alkoxy, halogen, trifluoromethyl, nitro or cyano or a phenylalkyl group which is unsubstituted or substituted by C$_1$–C$_4$-alkyl, C$_1$–C$_4$-alkoxy, halogen, trifluoromethyl, nitro or cyano in the aryl portion and which is C$_1$–C$_4$-alkyl in the alkyl portion, or in which R denotes a cycloalkyleneimino, cycloalkenylamino or cycloalkadienyleneimino group which has a total of 4 to 7 ring members and is unsubstituted or substituted by one or two C$_1$–C$_4$-alkyl groups, and R$^3$ denotes a C$_1$ to C$_4$ alkyl group which is unsubstituted or substituted by C$_1$–C$_4$-alkoxy, halogen, trifluoromethyl, cyano or nitro or a C$_2$ to C$_6$ alkenyl group.

2. A compound according to claim 1, in which

X denotes an oxygen or sulphur atom,

Z denotes a straight-chain or branched alkylene group with 1 to 6 carbon atoms,

R denotes an NHR$^1$ or NR$^1$R$^2$ group, in which

R$^1$ and R$^2$ are identical or different and denote a C$_1$ to C$_6$ alkyl group, on in which R denotes a cycloalkyleneimino group which has a total of 5 to 7 ring members and unsubstituted or substituted by one or two C$_1$ to C$_4$ alkyl groups and R$^3$ denotes a C$_1$ to C$_4$ alkyl group.

3. A pharmaceutical composition containing as an active ingredient an anthelmintically effective amount of a compound according to claim 1 in admixture with a solid, liquid or liquefied gaseous diluent.

4. A pharmaceutical composition containing as an active ingredient an anthelmintically effective amount of a compound according to claim 1 in the form of a sterile or physiologically isotonic aqueous solution.

5. A composition according to claim 3 containing from 0.5 to 90% by weight of the said active ingredient.

6. A medicament in dosage unit form comprising an anthelmintically effective amount of a compound according to claim 1 and an inert pharmaceutical carrier.

7. A medicament of claim 6 in the form of tablets, pills, dragees, capsules, ampules, or suppositories.

8. A method of combating helminthiases in warmblooded animals which comprises administering to the animals an anthelmintically effective amount of an active compound according to claim 1 either alone or in admixture with a diluent or in the form of a medicament.

9. A method according to claim 8 in which the active compound is administered in an amount of 1 to 100 mg per kg body weight per day.

10. A method according to claim 8 or 9 in which the active compound is administered orally or parenterally.

* * * * *